(12) United States Patent
Blondel et al.

(10) Patent No.: US 8,457,790 B2
(45) Date of Patent: Jun. 4, 2013

(54) ROBOTIC CALIBRATION METHOD

(75) Inventors: Lucien Blondel, Montepellier (FR);
Jackson R. Heavener, Warsaw, IN (US)

(73) Assignee: Zimmer, Inc., Warsaw ( * ) Notice: Subject to any disclaimer, the term of this patent is extended or adjusted under 35 U.S.C. 154(b) by 856 days.

(21) Appl. No.: 12/210,165

(22) Filed: Sep. 12, 2008

(65) Prior Publication Data
US 2009/0076655 A1 Mar. 19, 2009

Related U.S. Application Data

(60) Provisional application No. 60/972,345, filed on Sep. 14, 2007.

(51) Int. Cl.
G05B 19/04 (2006.01)

(52) U.S. Cl.
USPC .......................................................... 700/254

(58) Field of Classification Search
USPC .......................................................... 701/254
See application file for complete search history.

(56) References Cited

U.S. PATENT DOCUMENTS

| 5,402,582 | A | 4/1995 | Raab |
| 5,611,147 | A | 3/1997 | Raab |
| 5,978,748 | A | 11/1999 | Raab |
| 6,131,299 | A | 10/2000 | Raab et al. |
| 6,202,031 | B1 * | 3/2001 | Campbell et al. ................ 702/95 |
| 6,285,920 | B1 * | 9/2001 | McGee et al. ................ 700/254 |
| 6,321,137 | B1 * | 11/2001 | De Smet ........................ 700/245 |
| 6,408,252 | B1 | 6/2002 | De Smet |
| 6,812,665 | B2 * | 11/2004 | Gan et al. ................. 318/568.11 |
| 6,822,412 | B1 * | 11/2004 | Gan et al. ................. 318/568.19 |
| 7,174,651 | B2 | 2/2007 | Raab et al. |
| 2003/0200042 | A1 * | 10/2003 | Gan et al. ...................... 702/105 |
| 2004/0021876 | A1 * | 2/2004 | De Jonge et al. ............. 356/601 |
| 2004/0251866 | A1 * | 12/2004 | Gan et al. ................. 318/568.11 |
| 2007/0051179 | A1 * | 3/2007 | McMurtry et al. .............. 73/760 |
| 2007/0156157 | A1 | 7/2007 | Nahum et al. |
| 2008/0188986 | A1 * | 8/2008 | Hoppe .......................... 700/263 |

OTHER PUBLICATIONS

Article—Berthold K.P. Horn, Department of Electrical Engineering, University of Hawaii at Manoa, Honolulu, Hawaii "Closed-form solution of absolute orientation using unit quaternions", 1987 Optical Society of America.

* cited by examiner

Primary Examiner — James Trammell
Assistant Examiner — Michael D Lang
(74) Attorney, Agent, or Firm — Norton Rose Canada LLP

(57) ABSTRACT

A robot is characterized by an external measurement device. The robot generates a first point cloud of data. The external measurement device generates a second point cloud of data. These two points clouds are analyzed to determine an accuracy of the robot.

20 Claims, 6 Drawing Sheets

ROBOTIC CALIBRATION METHOD

RELATED APPLICATIONS

This application claims the benefit of U.S. Provisional Patent Application Ser. No. 60/972,345, filed Sep. 14, 2007, and titled ROBOT CALIBRATION METHOD, the disclosure of which is expressly incorporated by reference herein.

BACKGROUND

1. Field of the Disclosure

The present disclosure relates to calibration methods for computer assisted surgery systems. More particularly, the present disclosure relates to a calibration method for a robot used in a computer assisted surgery system.

2. Description of the Related Art

Calibration methods for robotic systems may be used to improve the accuracy of the robotic systems. The accuracy of surgical robots is important so that cut guides and other types of tools are properly positioned relative to anatomical structures. For instance, in knee replacement procedures, resections need to be accurately carried out for the artificial knee to function properly.

SUMMARY

The present disclosure provides a calibration method for a robot system. An exemplary robot system may be used in a computer assisted surgery system.

In an exemplary embodiment of the present disclosure, a method of obtaining calibration data for a robot system having an articulated arm is provided. The method comprising the steps of commanding said articulated arm of said robot system to position a calibration feature at a plurality of commanded points, said plurality of commanded points collectively being a first point cloud; for each of said commanded points, collecting with an external measurement device a measurement point corresponding to said position of said calibration feature, said plurality of measurement points collectively being a second point cloud; and adjusting one or more parameters of said robot system based on a comparison of said first point cloud and said second point cloud. In an example, said calibration feature is an end face of said articulated arm of said robot system. In another example, said calibration feature is a part of a calibration tool coupled to said end face of said robot system. In a variation thereof, said calibration feature is a sphere. In a further variation thereof, said external measurement device is a coordinate measurement machine and said step of collecting a measurement point corresponding to said position of said calibration feature includes the steps of collecting a calibration feature point cloud corresponding to an exterior of said sphere; and determining a center of said sphere from said calibration feature point cloud, said measurement point corresponding to said center of said sphere. In a further example, said external measurement device is a coordinate measurement machine. In yet another example, said step of adjusting said one or more parameters of robot system includes the steps of adjusting a kinematic model of said robot system; and subsequently adjusting one or more joint values of said robot system. in still another example, said first point cloud and said second point cloud are within a working volume of said robot system.

In another exemplary embodiment of the present disclosure, a method of obtaining calibration data for a robot system having an articulated arm is provided. The method comprising the steps of commanding said articulated arm of said robot system to position a calibration feature at a first point, said first point being included in a first point cloud in a first coordinate system; obtaining a first measurement point with an external coordinate measuring machine, said first measurement point corresponding to an actual position of said calibration feature and said first measurement point being included in a second point cloud in a second coordinate system; commanding said articulated arm of said robot system to position said calibration feature at a second point, said second point being included in said first point cloud in said first coordinate system; obtaining a second measurement point with said external coordinate measuring machine, said second measurement point corresponding to a second actual position of said calibration feature and said second measurement point being included in said second point cloud in said second coordinate system; commanding said articulated arm of said robot system to position said calibration feature at a third point, said third point being included in said first point cloud in said first coordinate system; obtaining a third measurement point with said external coordinate measuring machine, said third measurement point corresponding to a third actual position of said calibration feature and said third measurement point being included in said second point cloud in said second coordinate system; and adjusting one or more parameters of said robot system based on a comparison of said first point cloud and said second point cloud. In an example, said calibration feature is a sphere and said first measurement point is determined by the steps of while said calibration feature is positioned at said first point collecting a calibration feature point cloud corresponding to an exterior of said sphere; and determining a center of said sphere from said calibration feature point cloud, said first measurement point corresponding to said center of said sphere. In another example, the method further comprises the steps of obtaining a first direction of said robot with said external coordinate measuring machine when said calibration feature is positioned at said first position; obtaining a second direction of said robot with said external coordinate measuring machine when said calibration feature is positioned at said second position; and obtaining a third direction of said robot with said external coordinate measuring machine when said calibration feature is positioned at said third position. In a variation thereof, said calibration feature includes a plurality of spheres and said step of obtaining a first direction of said robot with said external coordinate measuring machine includes the steps of: collecting a first calibration feature point cloud corresponding to an exterior of a first sphere; determining a center of said first sphere from said first calibration feature point cloud; collecting a second calibration feature point cloud corresponding to an exterior of a second sphere; determining a center of said second sphere from said second calibration feature point cloud; collecting a third calibration feature point cloud corresponding to an exterior of a third sphere; and determining a center of said third sphere from said third calibration feature point cloud, wherein said first direction is perpendicular to a plane defined by said center of said first sphere, said center of said second sphere, and said center of said third sphere.

In a further exemplary embodiment of the present disclosure, a method of obtaining calibration data for a robot system having an articulated arm is provided. The method comprising the steps of: providing a calibration template with a plurality of calibration spots in a working volume of said robot system, said calibration spots forming a first point cloud in a first coordinate system; moving said articulated arm of said robot system to position a calibration feature at each of said calibration spots; recording a second plurality of points of a second point cloud in a second coordinate system, each of said second plurality of points corresponding to a position of said calibration feature at a respective calibration spot; and adjusting one or more parameters of said robot system based on a comparison of said first point cloud and said second point cloud. In an example, a coordinate measuring machine provides an indication of said first point cloud. In another example, said calibration spots are divots in a support and said calibration feature is a sphere coupled to an end face of said articulated arm. In a variation thereof, said recording step includes the steps of: placing said sphere in a first divot; sensing when said sphere is contacting a wall of said first divot; and storing said location of said sphere. In a further variation thereof, said location of said sphere when in said first divot is a first point of said second plurality of points. A further example, said step of adjusting said one or more parameters of robot system includes the steps of: adjusting a kinematic model of said robot system; and subsequently adjusting one or more joint values of said robot system.

In yet another exemplary embodiment of the present disclosure, a method of obtaining calibration data for a robot system having an articulated arm is provided. The method comprising the steps of providing a calibration template having a known geometry, said known geometry including a first point could; moving said articulated arm of said robot system to contact said calibration template with a calibration feature produce a second point cloud; and adjusting one or more parameters of said robot system based on a comparison of said first point cloud and said second point cloud. In an example, said calibration template includes at least one sphere of a known diameter which is included in said first point cloud.

Additional features and advantages of the present invention will become apparent to those skilled in the art upon consideration of the following detailed description of illustrative embodiments exemplifying the best mode of carrying out the invention as presently perceived.

BRIEF DESCRIPTION OF THE DRAWINGS

The above-mentioned and other features of the disclosure, and the manner of attaining them, will become more apparent and will be better understood by reference to the following description of embodiments of the disclosure taken in conjunction with the accompanying drawings, wherein.

Corresponding reference characters indicate corresponding parts throughout the several views. The exemplifications set out herein illustrate embodiments of the disclosure and such exemplifications are not to be construed as limiting the scope of the invention in any manner.

DETAILED DESCRIPTION

The present disclosure provides a calibration method for a robot used in a computer assisted surgery system. An exemplary robotic surgical system is described in U.S. patent application Ser. No. 11/610,728, entitled AN IMAGELESS ROBOTIZED DEVICE AND METHOD FOR SURGICAL TOOL GUIDANCE, filed Dec. 14, 2006, assigned to the assignee of the present application, the disclosure of which is hereby expressly incorporated herein by reference. This exemplary robotic surgical system is a computer controlled electromechanical multi-jointed arm which is used in a surgical operation environment for the spatial positioning and orientation of an instrument holder or tool guide to manually guide orthopaedic instruments.

Figure 1:
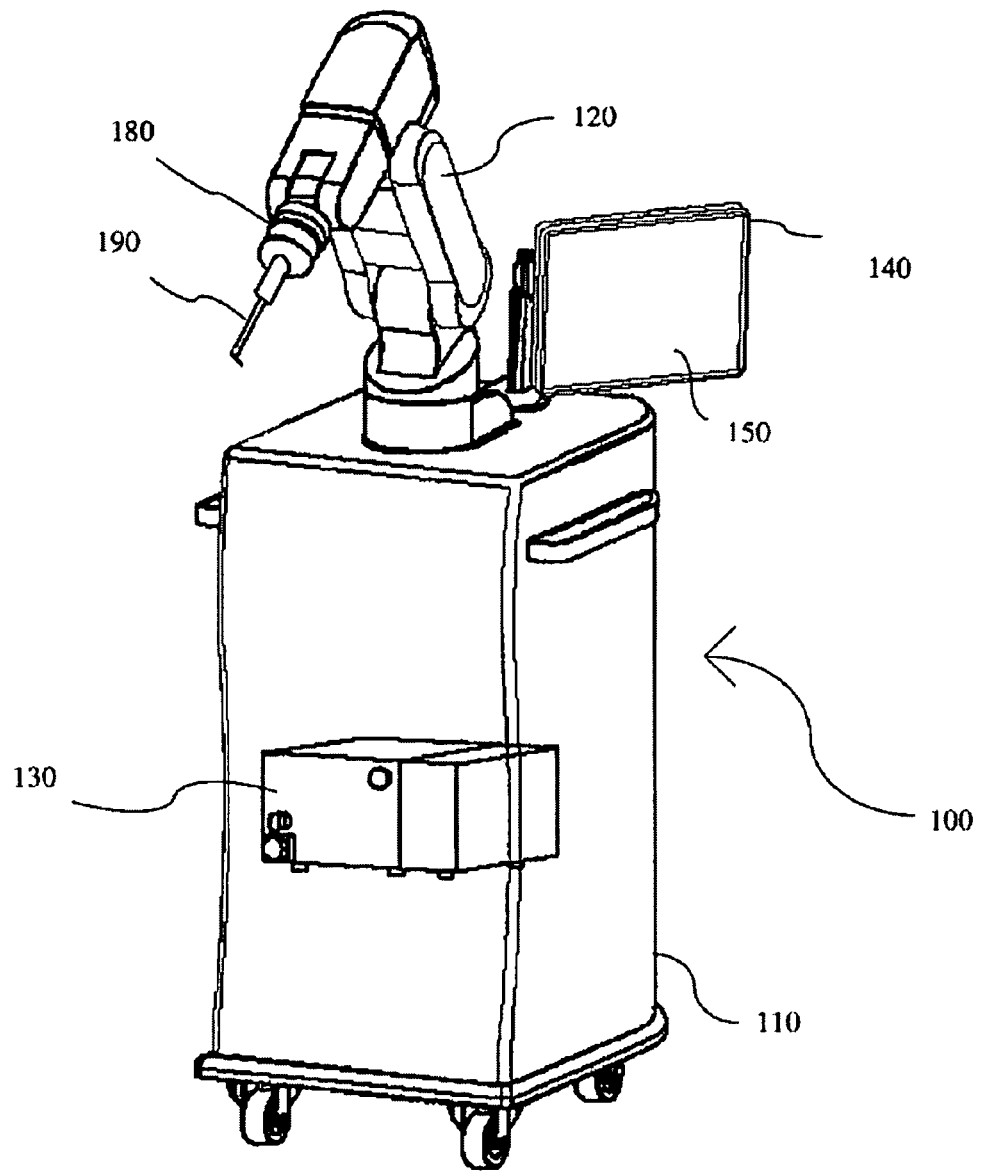
FIG. 1 illustrates an exemplary surgical robot system having a tool and a force sensor attached to an end face of an articulated arm of the surgical robot system.
Figure 2:
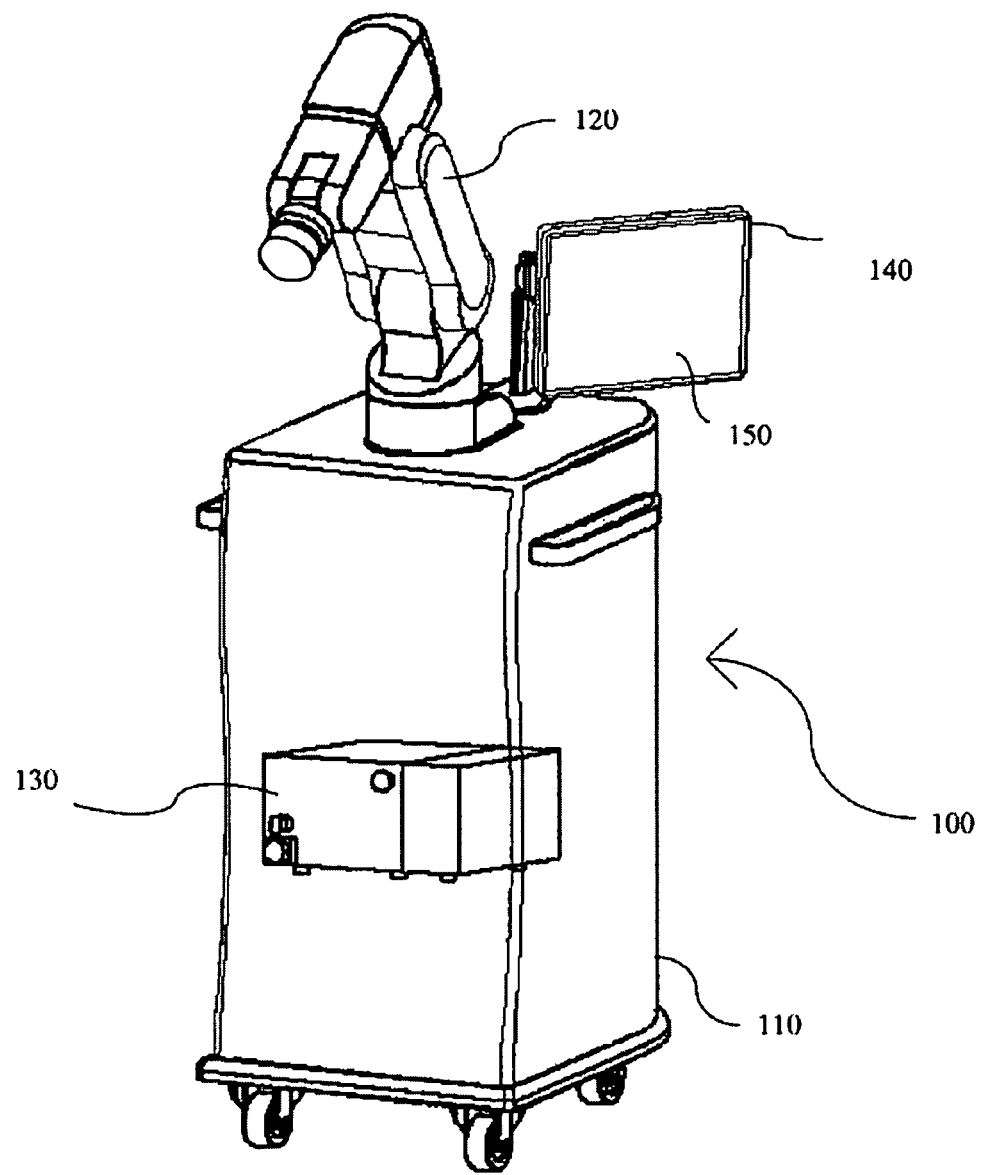
FIG. 2 illustrates the surgical robot of FIG. 1 with the tool and the force sensor removed from the end face of the articulated arm.

Referring to FIG. 1, an exemplary robotic surgical system 100 is shown. Robotic surgical system 100 includes a mobile base 110; an articulated arm 120; a control unit 130 positioned inside mobile base 110 which controls articulated arm 120. Control unit 130 also allows a surgeon or other operator to manually input data through the use of interface 150, such as a touch screen, a mouse, a joystick, a keyboard or similar device. In the illustrated example, a display monitor 140 is a touch screen which serves as interface 150. Tools 190 and/or force sensor 180 may be mounted to a mounting flange 122 (see FIG. 2) of articulated arm 120. Tools 190 include a pointing tool, a guiding tool, or a pointing and guiding tool. Exemplary tools include a pointer probe, a paddle probe, a saw, a mill, a cut guide, and other suitable types of tools.

In an exemplary embodiment, articulated arm 120 is a six joint arm. Each joint is provided with an encoder which measures its angular value. This data, combined with the known geometry of the six joints, allow computation of the position of the mounting flange 122 of articulated arm 120 (See FIG. 2) and the position of the tool or instrument 190 mounted to articulated arm 120.

Figure 3:
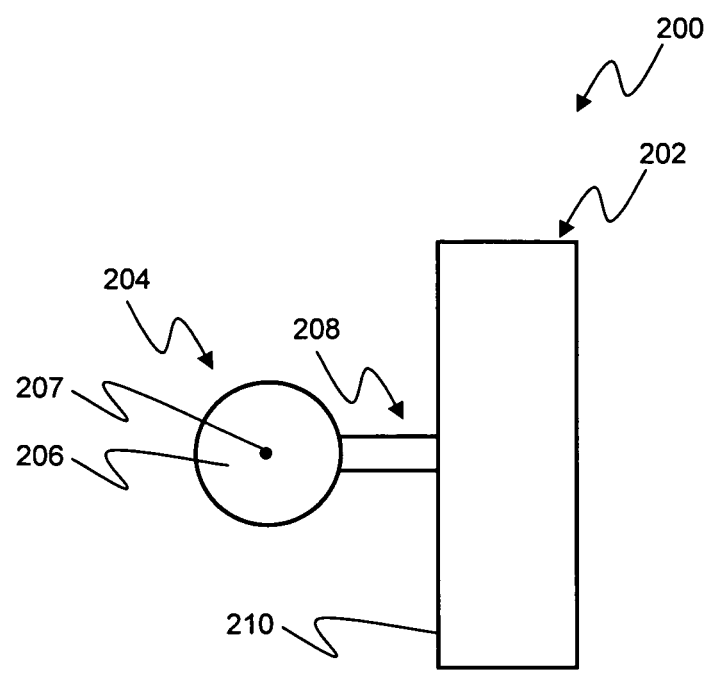
FIG. 3 is a side view of a first calibration tool which may be mounted to the end face of the articulated arm shown in FIG. 2.
Figure 4:
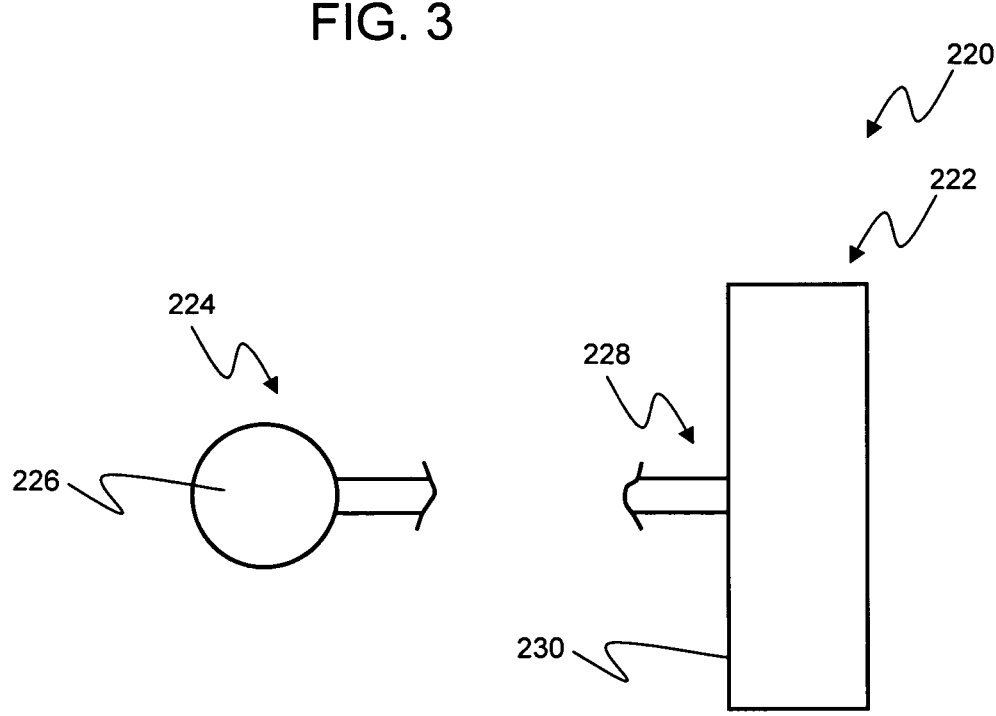
FIG. 4 is a side view of a second calibration tool which may be mounted to the end face of the articulated arm shown in FIG. 2.
Figure 5:
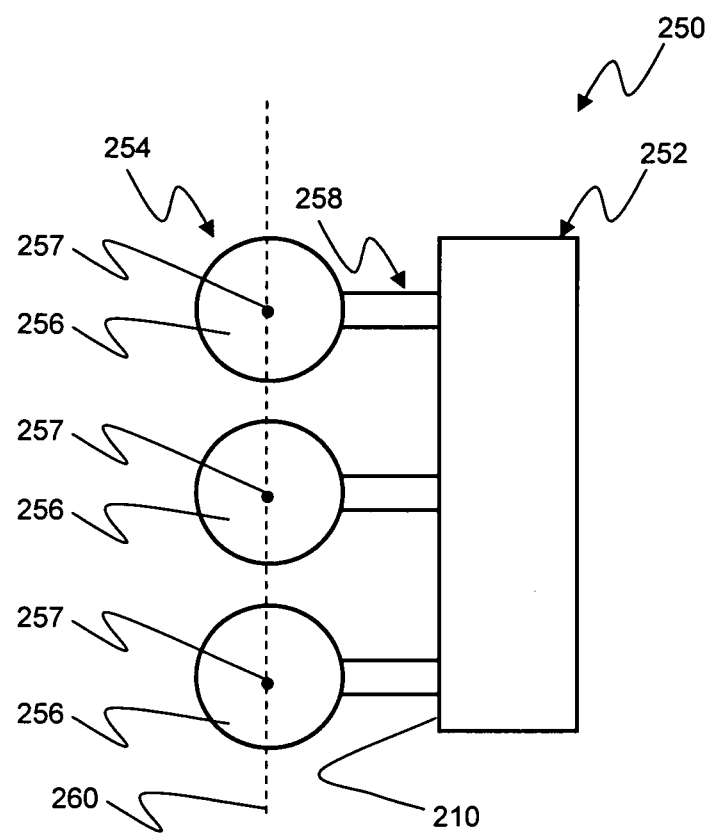
FIG. 5 is a side view of a third calibration tool which may be mounted to the end face of the articulated arm shown in FIG. 2.

FIGS. 3-5 illustrate various calibration tools which may be coupled to mounting flange 122. Referring to FIG. 3, a first calibration tool 200 is shown. Calibration tool 200 includes a base portion 202 which is attachable to mounting flange 122 through one or more couplers. Exemplary couplers include bolts which may pass into openings in base portion 202 and be threaded into mounting flange 122. First calibration tool 200 further supports a calibration probe 204. Calibration feature 204 is shown as a sphere 206. Other suitable calibration features may be used, such as cones, square. rectangle, cylinder, and other geometric shapes. Sphere 206 of calibration feature 204 is spaced apart from base portion 202 by a post 208. In one embodiment, sphere 206 is centered on a face surface 210 of base portion 202 which is circular.

Referring to FIG. 4, a second calibrating tool 220 is shown. Calibration tool 220 includes a base portion 222 which is attachable to mounting flange 122 through one or more couplers. Exemplary couplers include bolts which may pass into openings in base portion 222 and be threaded into mounting flange 122. Second calibrating tool 220 further supports a calibration feature 224. Calibration feature 224 is shown as a sphere 226. Other suitable calibration features may be used, such as cones, square. rectangle, cylinder, and other geometric shapes. Sphere 226 of calibration feature 224 is spaced apart from base portion 222 by a post 228. Post 228 is longer than post 208 and is used to provide calibration of angular deviations of robotic surgical system 100 during testing. In one embodiment, sphere 226 is centered on a face surface 230 of base portion 222 which is circular.

Referring to FIG. 5, a third calibration tool 250 is shown. Calibration tool 250 includes a base portion 252 which is attachable to mounting flange 122 through one or more couplers. Exemplary couplers include bolts which may pass into openings in base portion 252 and be threaded into mounting flange 122. Third calibration tool 250 further supports a calibration feature 254. Calibration feature 254 is shown as a plurality of spheres 256. Other suitable calibration features may be used, such as cones, square, rectangle, cylinder, and other geometric shapes. Spheres 256 of calibration feature 254 are spaced apart from base portion 252 by a plurality of posts 258. The centers of the three spheres define a plane 260. In one embodiment, plane 260 is parallel to a face surface 262 of base portion 252. As such, by knowing the orientation of plane 260, an orientation of face surface 262 and hence mounting flange 122 is known.

The calibration method of the present disclosure makes use of a point cloud determined by an external measuring device to calibrate robotic surgical system 100. The external measuring device has a greater accuracy than robotic surgical system 100. In one example, the accuracy of robotic surgical system 100 is about 0.25 mm and the accuracy of the external measuring device is about 0.04 mm. In one embodiment, the calibration method of the present disclosure utilizes as the external measuring device a portable coordinate measuring machine ("CMM"), such as a Titanium FaroArm®, available from FARO Technologies Inc. of Lake Mary, Fla., USA, for example. The Romer Infinite Arm manufactured by Romer Inc. of Wixom, Mich., USA is yet another example of a CMM. The CMM may use CAM2 Measure metrology software to calculate the coordinates of the probe of the portable CMM (another option is PC-DMIS software).

Exemplary CMM are disclosed in U.S. Pat. Nos. 5,402, 582; 5,611,147; 5,978,748; 6,131,299; and 7,174,651, the disclosures of which are expressly incorporated by reference herein. The CMM may be attached to a frame of robotic surgical system 100 to ensure that the CMM and the robotic surgical system 100 have the same coordinate reference system. However, the CMM and robotic surgical system 100 may also be separated and the use of a standard or other non-portable CMM may be used which can be aligned with the coordinate system of robotic surgical system 100.

Figure 6:
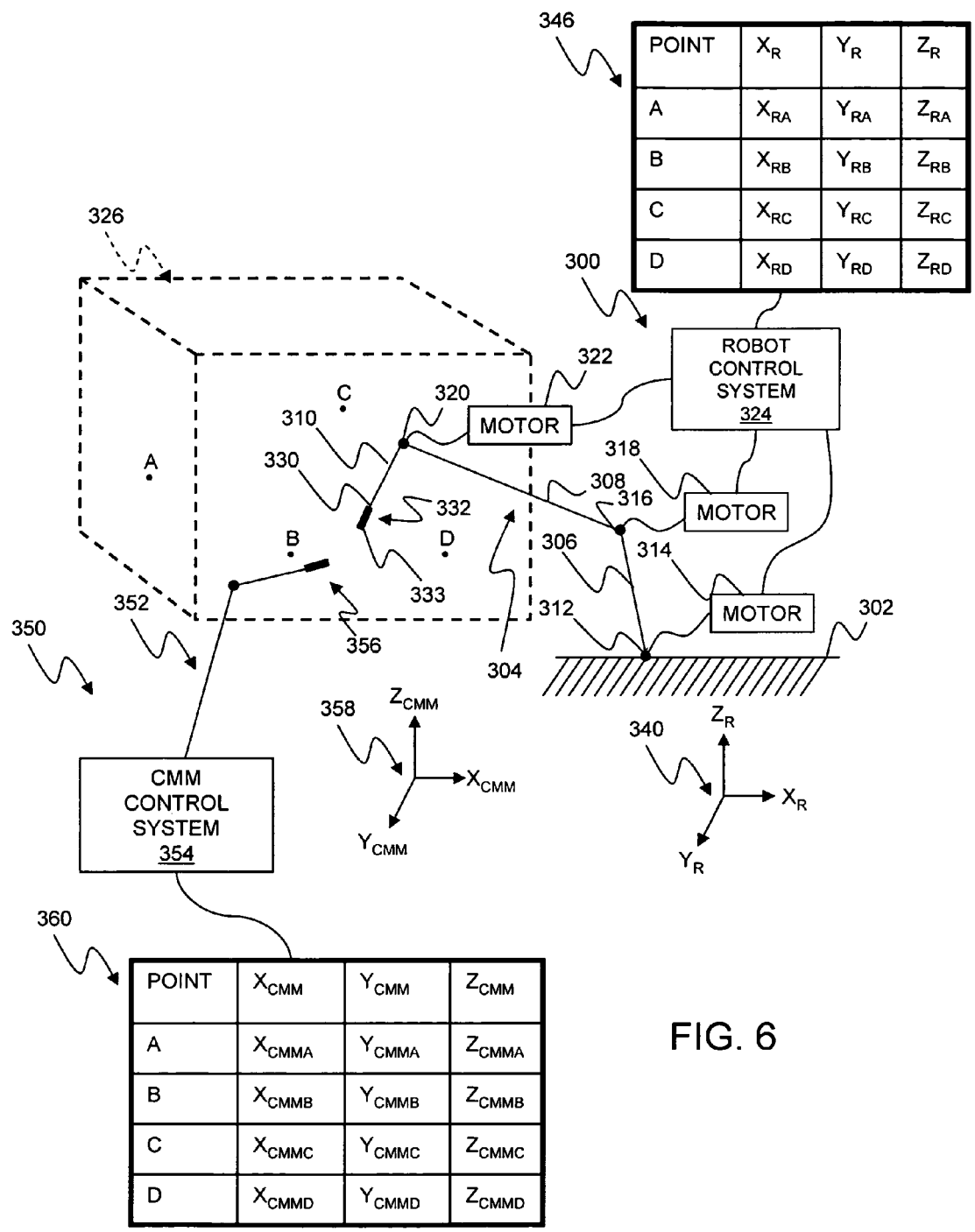
FIG. 6 is a representative view of a surgical robot system and a CMM each positionable within a working volume.
Figure 7:
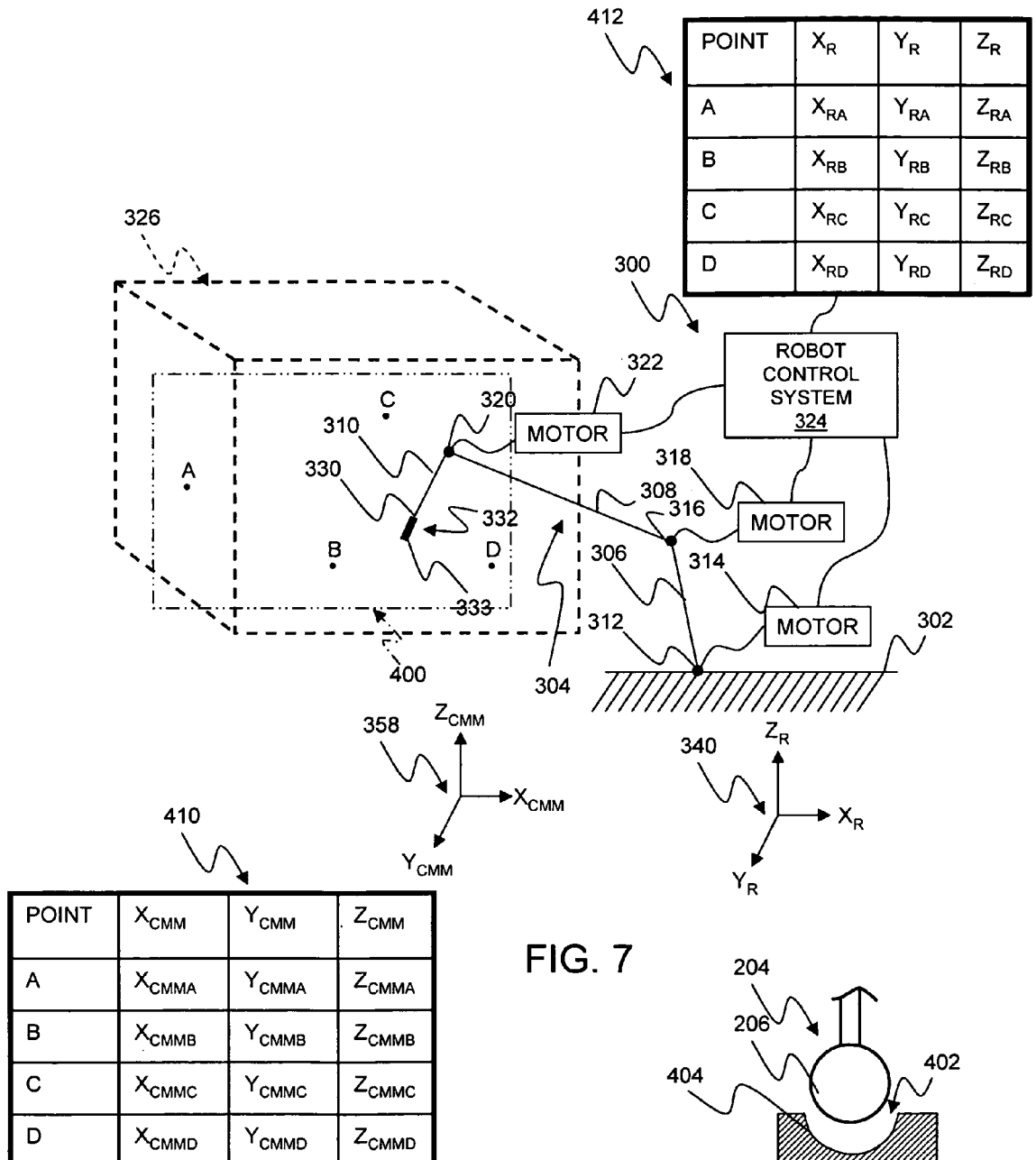
FIG. 7 is a representative view of the surgical robot system of FIG. 6 interacting with a calibration template positioned within the working volume.

Two exemplary calibration methods are provided in FIGS. 6 and 7, respectively. Referring to FIG. 6, a robotic surgical system 300 is represented. Robotic surgical system 300 includes a support 302 to which an articulated arm 304 is coupled. The articulated arm 304 has several joints having position encoders therein. In one embodiment, the robotic arm has six joints with six corresponding position encoders to define six axes of movement.

In the illustrated representation, articulated arm 304 includes three movable links 306, 308, and 310. Link 306 is movably coupled to support 302 through a first joint 312. First joint 312 is one of a rotational joint, whereby link 306 is rotatable relative to support 302; a translational joint, whereby link 306 is translatable relative to support 302; or a combination of rotational joint and a translational joint. The movement of link 306 relative to support 302 is controlled by a motor 314. An exemplary motor is an electric motor. Link 308 is movably coupled to link 306 through a second joint 314. Second joint 314 is one of a rotational joint, whereby link 308 is rotatable relative to link 306; a translational joint, whereby link 308 is translatable relative to link 306; or a combination of rotational joint and a translational joint. The movement of link 308 relative to link 306 is controlled by a motor 318. An exemplary motor is an electric motor. Link 310 is movably coupled to link 308 through a third joint 320. Third joint 320 is one of a rotational joint, whereby link 310 is rotatable relative to link 308; a translational joint, whereby link 310 is translatable relative to link 308; or a combination of rotational joint and a translational joint. The movement of link 310 relative to link 308 is controlled by a motor 322. An exemplary motor is an electric motor.

Motors 314, 318, and 322 are controlled by a robot control system 324. Robot control system 324, in one embodiment, includes a computing device executing software to control the operation of robotic surgical system 300 including the movement of support 302. An exemplary robot control system 324 is control unit 130 of robotic surgical system 100.

The movement of support 302 may locate an end 330 of support 302 at a point in a working volume 326. Working volume 326 is shown as a cube, but may take on any shape based on the kinematics of robotic surgical system 300. A tool 332 may be coupled to end 330. Robot control system 324 by knowing the offset of a tool portion 333 (such as sphere 206) of tool 332 may locate the tool portion 333 of tool 332 in the robot coordinate system 340. In addition to a location in working volume 326, robot control system 324 may control an orientation of link 310, such that not only is the location of end 330 or the tool portion of tool 332 controlled, but also the direction link 310 takes in placing end 330 or the tool portion of tool 332 at that location.

Robot control system 324 records the location end 330 or the tool portion of tool 332 and the direction of link 310 in a robot coordinate system 340. Robot coordinate system 340 is shown as a Cartesian coordinate system, but may be any type of coordinate system. Of course, robot control system 324 may also keep track of the location of joint 312, joint 316, and joint 320 along with the direction of link 306 and link 308.

Also represented in FIG. 6 is a CMM 350. CMM 350 includes an articulated arm 352 and a CMM control system 354 which records the position of an end effector 356 of articulated arm 352. CMM control system 354 records the position of end effector 356 in a CMM coordinate system 358. CMM coordinate system 358 is shown as a Cartesian coordinate system, but may be any type of coordinate system.

The robotic surgical system 300 may move the joints 312, 316, and 320 according to a desired location of the tool portion of tool 332 using information acquired during a landmarking procedure. To ensure the robotic surgical system can accurately and repeatably identify the location of the tool portion of tool 332, the articulated arm 304 is subjected to a calibration routine to verify that the desired location of the tool portion of tool 332 is accurate. The CMM 350 may be used to either confirm sufficient accuracy or provide data inputs to adjust a set of calibration parameters to modify the position encoders/joints of the robotic arm such that the end effector is located in a sufficiently accurate position.

In the representation illustrated in FIG. 6, articulated arm 304 is calibrated by moving a tool portion of tool 332 to a number of known reference positions, illustratively reference points A, B, C, and D, throughout the working volume 326 of the articulated arm 304. The movement from A, B, C, and to D is a trajectory of the tool portion of tool 332. The reference positions, illustratively A, B, C, D, represent a theoretical point cloud 346 in the robot coordinate system 340 in which the articulated arm 304 is intended to position itself.

At each reference position, the location of the tool portion of tool 332 is characterized using the CMM system 350. The measurements taken by the CMM at each reference position represent an actual point cloud 360 in the CMM coordinate system 358. Point cloud 360 is a measurement of the actual position of the tool portion of tool 332 and is used to characterize the error in point cloud 346. This error may be used to better calibrate robotic surgical system 300 to reduce the error in future movements of articulated arm 304. This error may be determined by a comparison of point cloud 346 and point cloud 360 wherein one or more of a translation of robot coordinate system 340 along one or more of its axes is identified, a rotation of robot coordinate system 340 is identified, a scale difference is identified, or a combination thereof. Based on these errors, the parameters of robot control system 324 which position encoders/joints may be adjusted to optimize accuracy of the positioning of the tool portion of tool 332. Further, an iterative mathematical algorithm which uses D-H (Denavit-Hartenberg) parameters, as are well-known in the field of robotics, to optimize the kinematics model of the robotic surgical system 300. D-H parameters may be used to define the coordinate space around a robotic arm having multiple joints with multiple degrees of freedom and thereafter used to calibrate the joint offsets of the joints of the robotic arm. In one embodiment, point cloud 360 is communicated to robot control system 324 which characterizes the error in point cloud 346.

In order to evaluate the accuracy of robotic surgical system 300, point cloud 346 and point cloud 360 must be resolved to share the same coordinate system. In one example, this shared coordinate system is coordinate system 340. In one embodiment, point cloud 360 is fit to point cloud 346 to determine the error in the position of the tool portion of tool 332 through a closed form method. One closed form method of determining the error in the position of the tool portion of tool 332 is disclosed in Berthold K. P. Horn's "Closed-Form solution of absolute orientation using unit quaternions," the disclosure of which is expressly incorporated by reference herein. In alternative embodiment, other methods may be used including iterative least squares methods. Once point cloud 346 and point cloud 360 have been resolved, given knowledge of the base kinematic model (generally referred to as D-H Parameters), the robot kinematic model may be optimized to minimize for example, the positional inaccuracy. The new kinematic model (updated parameters) may then be used to correct the robot systems joint values to effectively further correct the accuracy of the robot. Once these steps have been taken, the robot system may again be tested through the same trajectory with the external measuring device. In one embodiment, forty points (as opposed to the illustrated 4 points) are provided as trajectory points.

Appendix A provided in U.S. Provisional Patent Application Ser. No. 60/972,345 includes further details and description regarding one such methodology used to calibrate the robotic surgical system.

In one embodiment, calibration tool 200 is used as tool 332 and sphere 206 is the tool portion of calibrating tool 200. Robot control system 324 attempts to position calibrating tool 200 such that a center 207 of sphere 206 is positioned at the respective points A, B, C, and D. When CMM system 350 is used to determine the actual location of center 207, end effector 356 digitizes multiple positions on the exterior of sphere 206. A sphere is then fit to digitized points to produce a determined point for center 207. Referring to FIG. 6, for point A this determined point is $x_{CMMA}$, $y_{CMMA}$, and $z_{CMMA}$. The diameter of sphere 206 is a known value. As such, by digitizing sphere 206 and determining the center 207 and thus also the diameter with CMM system 350 the accuracy of CMM system 350 may also be checked. For instance, if it is known that sphere 206 has a diameter of 0.5 inches then if the diameter of the sphere determined by CMM system 350 is offset from 0.5 inches by more than a threshold amount, such as 0.05 inches, then there may be a problem with the calibration of CMM system 350. In this situation, CMM system 350 should be recalibrated.

In the case wherein the direction of link 310 is also important, a direction of link 310 may be determined by CMM system 350 with calibrating tool 250 being used as tool 332. CMM system 350 is used to digitize each of spheres 256 separately to determine centers 257. The three centers 257 define a plane 260 which is at a known orientation relative to end face 262 of calibrating tool 250, illustratively parallel. As such, by knowing the orientation of plane 260 a direction of link 310 is readily determinable.

In one embodiment, calibrating tool 220 is used as tool 332 and sphere 226 is the tool portion of calibrating tool 220. calibrating tool 220 is used in a similar manner as calibrating tool 200. However, by having sphere 226 a greater distance away from base portion 222 than sphere 206 is from base portion 202 angular errors in the positioning of link 310 are magnified and hence easier to detect.

In one embodiment, instead of digitizing a calibration tool to determine the location of the robotic system 100, a center position of end face 122 is digitized to determine the location of robotic system 100. In one example, end face 122 includes a divot or other feature that is digitized to determine a center position of end face 122.

Figure 8:
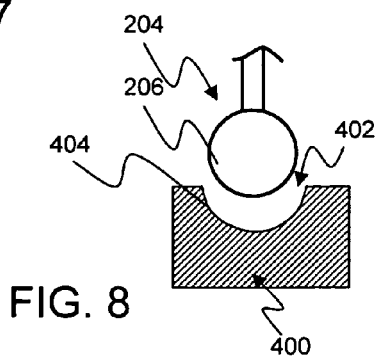
FIG. 8 is a representative view of a sphere calibration tool of the surgical robot system of FIG. 7 being positioned in a calibration spot of the calibration template.

Referring to FIGS. 7 and 8, a variation on the calibration of robotic surgical system 300 is shown. In FIG. 7, robotic surgical system 300 is again shown. Also represented is a calibration template 400 is shown. Calibration template 400 includes a plurality of calibration spots 402 (see FIG. 8). In the illustrated embodiment, plurality of calibration spots 402 are generally spherical divots 404 which are sized to generally match a diameter of sphere 206 of calibrating tool 200. In this embodiment, CMM system 350 is used to digitize calibration template 400 to determine a center of each of divots 404. These centers from an actual point cloud 410 in CMM coordinate system 358. An operator places sphere 206 of robotic surgical system 300 into each divot 404 and the position of sphere 206 is recorded as a part of point cloud 412. In one example, force sensor 180 provides a notification to robot control system 324 of when sphere 206 is positioned in divot 404. These two point clouds are used in a similar manner as point cloud 346 and point cloud 360 to determine the accuracy of robotic surgical system 300. In one embodiment, calibration spots 402 restrict an orientation of articulated arm 304. In one example, calibration spots 402 are cylindrical holes, polygonal holes, or other features and the corresponding calibration tool is pin or other protrusion which requires mounting flange 122 to be oriented along a specified direction for the calibration tool to be received by the corresponding calibration spots 402. For example, a cylindrical pin will be able to bottom out against a bottom surface of a cylindrical hole when the axis of the cylindrical pin is generally aligned with the axis of the cylindrical hole.

Calibration template 400 is generally an object having a geometry characterized by an external measuring machine such that it has a known geometry. A first collection of these known points is a first point cloud. In one embodiment, robotic surgical system 300 is used to contact and record its position at a plurality of points along the known geometry. These points are a second point cloud. These two point clouds are used in a same manner as point cloud 346 and point cloud 360 to determine the accuracy of robotic surgical system 300. In one example, the calibration template 400 is one or more spheres of known diameter and the calibration feature of the arm 304 is a pointer or other device for contacting the sphere.

Although described throughout with reference to a surgical robotic system, the calibration techniques described herein may be used with other types of robot systems.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A method of obtaining calibration data for a robot system having an articulated arm, the method comprising the steps of:
    providing a calibration template having a plurality of calibration spots formed in the calibration template at predetermined fixed positions therein, the calibration spots comprising divots in the calibration template, the calibration spots having a known geometry defining a first point cloud as determined by an external measurement device;
    commanding said articulated arm of said robot system to position a calibration feature coupled to the articulated arm at a plurality of commanded points corresponding to said calibration spots of the calibration template, the calibration feature having a shape which corresponds to and is received within said divots of the calibration template;
    for each of said commanded points, determining with the robot system a measurement point corresponding to said position of said calibration feature, said plurality of measurement points collectively being a second point cloud; and
    adjusting one or more parameters of said robot system based on a comparison of said first point cloud and said second point cloud.

2. The method of claim 1, wherein said calibration feature is an end face of said articulated arm of said robot system.

3. The method of claim 1, wherein said calibration feature is a part of a calibration tool coupled to said end face of said robot system.

4. The method of claim 3, wherein said calibration feature is a sphere.

5. The method of claim 4, wherein said external measurement device is a coordinate measurement machine and said step of determining a measurement point corresponding to said position of said calibration feature includes the steps of:
    collecting a calibration feature point cloud corresponding to an exterior of said sphere; and
    determining a center of said sphere from said calibration feature point cloud, said measurement point corresponding to said center of said sphere.

6. The method of claim 1, wherein said external measurement device is a coordinate measurement machine.

7. The method of claim 1, wherein said step of adjusting said one or more parameters of robot system includes the steps of:
    adjusting a kinematic model of said robot system; and
    subsequently adjusting one or more joint values of said robot system.

8. The method of claim 1, wherein said first point cloud and said second point cloud are within a working volume of said robot system.

9. The method of claim 1, wherein the divots of the calibration template are generally spherical and configured to receive therein a correspondingly shaped sphere of the calibration feature.

10. A method of obtaining calibration data for a robot system having an articulated arm, the method comprising the steps of:
    providing a calibration template having a plurality of calibration spots formed in the calibration template at predetermined fixed positions therein, said calibration spots defining divots in the calibration template, each of the calibration spots having a known position determined by an external coordinate measuring machine, the known positions forming a first point cloud in a first coordinate system;
    commanding said articulated arm of said robot system to position a calibration feature coupled to the articulated arm at a first one of said calibration spots, the calibration feature having a shape which corresponds to and is received within said divots of the calibration template;
    obtaining a first measurement point corresponding to an actual position of said calibration feature and said first measurement point being included in a second point cloud in a second coordinate system;
    commanding said articulated arm of said robot system to position said calibration feature at a second one of said calibration spots;
    obtaining a second measurement point corresponding to a second actual position of said calibration feature and said second measurement point being included in said second point cloud in said second coordinate system;
    commanding said articulated arm of said robot system to position said calibration feature at a third one of said calibration spots;
    obtaining a third measurement point corresponding to a third actual position of said calibration feature and said third measurement point being included in said second point cloud in said second coordinate system; and
    adjusting one or more parameters of said robot system based on a comparison of said first point cloud and said second point cloud.

11. The method of claim 10, wherein said calibration feature is a sphere and said first measurement point is determined by the steps of:
    while said calibration feature is positioned at said first one of said calibration spots, collecting a calibration feature point cloud corresponding to an exterior of said sphere; and
    determining a center of said sphere from said calibration feature point cloud.

12. The method of claim 10, further comprising the steps of:
    obtaining a first direction of said robot with said external coordinate measuring machine when said calibration feature is positioned at said first one of said calibration spots;
    obtaining a second direction of said robot with said external coordinate measuring machine when said calibration feature is positioned at said second one of said calibration spots; and
    obtaining a third direction of said robot with said external coordinate measuring machine when said calibration feature is positioned at said third one of said calibration spots.

13. The method of claim 12, further comprising:
providing said calibration feature with at least three spheres; and
wherein said step of obtaining a first direction of said robot with said external coordinate measuring machine includes the steps of:
collecting a first calibration feature point cloud corresponding to an exterior of a first sphere; determining a center of said first sphere from said first calibration feature point cloud; collecting a second calibration feature point cloud corresponding to an exterior of a second sphere; determining a center of said second sphere from said second calibration feature point cloud; collecting a third calibration feature point cloud corresponding to an exterior of a third sphere; and determining a center of said third sphere from said third calibration feature point cloud, wherein said first direction is perpendicular to a plane defined by said center of said first sphere, said center of said second sphere, and said center of said third sphere.

14. The method of claim 10, wherein the first measurement point is determined independent of the position of the articulated arm of the robot system.

15. A method of obtaining calibration data for a robot system having an articulated arm, the method comprising the steps of:
providing a calibration template with a plurality of calibration spots in a working volume of said robot system, said calibration spots defining divots in the calibration template, said calibration spots being formed in the calibration template at predetermined fixed positions therein and having a known geometry forming a first point cloud in a first coordinate system as determined by an external measurement device;
moving said articulated arm of said robot system to position a calibration feature coupled to the articulated arm at each of said calibration spots of the calibration template, the calibration feature having a shape which corresponds to and is received within said divots of the calibration template;
recording a second plurality of points of a second point cloud in a second coordinate system, each of said second plurality of points corresponding to a position of said calibration feature at a respective calibration spot as determined by the robot system; and
adjusting one or more parameters of said robot system based on a comparison of said first point cloud and said second point cloud.

16. The method of claim 15, wherein said divots are formed in a support and said calibration feature is a sphere coupled to an end face of said articulated arm.

17. The method of claim 16, wherein said recording step includes the steps of:
placing said sphere in a first divot;
sensing when said sphere is contacting a wall of said first divot; and
storing said location of said sphere.

18. The method of claim 17, wherein said location of said sphere when in said first divot is a first point of said second plurality of points.

19. The method of claim 15, wherein said step of adjusting said one or more parameters of robot system includes the steps of:
adjusting a kinematic model of said robot system; and
subsequently adjusting one or more joint values of said robot system.

20. The method of claim 15, wherein the first point cloud includes at least three non-linear points and the second point cloud including at least three non-linear points.

* * * * *